United States Patent
Mikami

(10) Patent No.: US 9,664,605 B2
(45) Date of Patent: May 30, 2017

(54) FUEL DENSITY DETECTION DEVICE

(71) Applicant: DENSO CORPORATION, Kariya, Aichi-pref. (JP)

(72) Inventor: Naoki Mikami, Takahama (JP)

(73) Assignee: DENSO CORPORATION, Kariya (JP)

( * ) Notice: Subject to any disclaimer, the term of this patent is extended or adjusted under 35 U.S.C. 154(b) by 173 days.

(21) Appl. No.: 14/830,136

(22) Filed: Aug. 19, 2015

(65) Prior Publication Data

US 2016/0061705 A1    Mar. 3, 2016

(30) Foreign Application Priority Data

Sep. 2, 2014 (JP) .................. 2014-178097

(51) Int. Cl.
*F02D 19/06* (2006.01)
*G01N 9/26* (2006.01)

(52) U.S. Cl.
CPC ............. *G01N 9/26* (2013.01); *F02D 19/061* (2013.01); *F02D 2200/0602* (2013.01); *F02D 2200/0612* (2013.01)

(58) Field of Classification Search
CPC ..... F02D 2200/0602; F02D 2200/0612; F02D 19/061; F02D 41/04; F02D 41/182; F02D 41/345; F02D 41/3809; F02D 2200/0604; F02D 2200/0616; F02D 2250/04; G01N 33/2852
See application file for complete search history.

(56) References Cited

U.S. PATENT DOCUMENTS

| 7,552,709 B2 * | 6/2009 | Fujii ................... F02D 41/2438 123/299 |
| 7,793,536 B2 * | 9/2010 | Schenck Zu Schweinsberg ....... F02D 35/023 73/114.55 |
| 9,127,608 B2 * | 9/2015 | Ito ....................... F02D 41/1497 |
| 9,157,389 B2 * | 10/2015 | Nonoyama ......... F02D 41/0025 |

(Continued)

FOREIGN PATENT DOCUMENTS

| JP | 2006125371 A * | 5/2006 | ......... F02D 41/2438 |
| JP | 2007-303395 A | 11/2007 | |

(Continued)

OTHER PUBLICATIONS

English language machine translation of JP 2007-303395A, originally published on Nov. 2007.*

(Continued)

*Primary Examiner* — David A Rogers

(57) ABSTRACT

A pulsation detection unit detects, as an actual characteristic, a pulsation frequency of a pressure pulsation, which is caused in fuel pressure, or a physical quantity corresponding to the pulsation frequency, according to a sensor signal from a pressure sensor. The pressure sensor detects a fuel pressure of fuel supplied to a fuel injection valve, which is equipped to an internal combustion engine. A storage unit stores, as a reference characteristic, a reference frequency of a predetermined reference pulsation or a physical quantity corresponding to the reference frequency. A density detection unit detects a fuel density according to a quantity of deviation between the reference characteristic, which is stored in the storage unit, and the actual characteristic, which is detected with the pulsation detection unit.

10 Claims, 4 Drawing Sheets

(56) References Cited

U.S. PATENT DOCUMENTS

| | | | |
|---|---|---|---|
| 9,394,847 B2* | 7/2016 | Sukegawa | F02D 13/0219 |
| 9,546,992 B2* | 1/2017 | Yamada | F02D 41/28 |
| 2008/0289405 A1* | 11/2008 | Schenck Zu Schweinsberg | F02D 35/023 73/114.52 |
| 2010/0319445 A1* | 12/2010 | Yamada | F02D 41/22 73/114.51 |
| 2012/0253639 A1* | 10/2012 | Nonoyama | F02D 41/0025 701/103 |
| 2013/0311063 A1* | 11/2013 | Ito | F02D 41/1497 701/103 |
| 2014/0158092 A1* | 6/2014 | Sukegawa | F02D 13/0219 123/480 |
| 2015/0330960 A1* | 11/2015 | Christensen | F02D 41/3845 73/37 |

FOREIGN PATENT DOCUMENTS

| | | |
|---|---|---|
| JP | 2010-071187 A | 4/2010 |
| JP | 2014-148906 A | 8/2014 |

OTHER PUBLICATIONS

English language machine translation of JP 2010-071187A, originally published on Apr. 2010.*
English language machine translation of JP 2014-148906A, originally published on Aug. 2014.*

* cited by examiner

FUEL DENSITY DETECTION DEVICE

CROSS REFERENCE TO RELATED APPLICATION

This application is based on reference Japanese Patent Application No. 2014-178097 filed on Sep. 2, 2014, the disclosure of which is incorporated herein by reference.

TECHNICAL FIELD

The present disclosure relates to detection of a fuel density.

BACKGROUND

In general, in a state where a density of fuel differs, a lubricity of fuel and a combustion property of fuel differ correspondingly. Therefore, it may be demanded to detect a density of fuel and to perform an engine control according to the detected density of fuel. For example, Patent Document 1 may disclose that a cycle of a pressure pulsation, which is caused in fuel pressure when a fuel injection valve injects fuel, changes correspondingly to change in a density of fuel. For example, a pressure sensor device may be employed to detect change in a pressure pulsation. In this case, a physical quantity, which includes a frequency of a pressure pulsation or a cycle relevant to the frequency, may be detected as an actual characteristic according to a sensor signal from the pressure sensor device. The present way may enable detection of a density of fuel without using a density sensor.

Patent Document 1

Publication of unexamined Japanese patent application No. 2010-71187

In a configuration to detect an actual characteristic according to a sensor signal of a pressure sensor device, it may be assumable to employ, for example, the following way. Specifically, a frequency of a pressure pulsation or a cycle of a pressure pulsation may be first detected according to a length between peaks in a waveform of a pressure pulsation. Subsequently, a fuel density corresponding to the actual characteristic, such as the detected frequency of the pressure pulsation or the detected cycle of the pressure pulsation, may be retrieved from, for example, a data map and/or the like.

It is noted that, when the sensor signal of the pressure sensor contains a noise, the position of the peak may be shifted. Consequently, a detection accuracy of the actual characteristic of the pressure pulsation may decrease. Thus, a detection accuracy of the actual characteristic of the pressure pulsation may decrease in a configuration to detect a density of fuel according to only an actual characteristic of a pressure pulsation, which is detected with a pressure sensor device. Consequently, the decrease in the detection accuracy may directly result in decrease in a detection accuracy of a density of fuel.

SUMMARY

It is an object of the present disclosure to enhance a detection accuracy of a fuel density regardless of usage of a density sensor device.

According to one aspect of the present disclosure, a fuel density detection device comprises a pulsation detection unit configured to detect, as an actual characteristic, a pulsation frequency of a pressure pulsation, which is caused in a fuel pressure, or a physical quantity, which corresponds to the pulsation frequency, according to a sensor signal from a pressure sensor. The pressure sensor is configured to detect the fuel pressure of fuel supplied to a fuel injection valve, which is equipped to an internal combustion engine. The fuel density detection device further comprises a storage unit configured to store, as a reference characteristic, a reference frequency of a predetermined reference pulsation or a physical quantity, which corresponds to the reference frequency. The fuel density detection device further comprises a density detection unit configured to detect a fuel density according to a quantity of deviation between the reference characteristic, which is stored in the storage unit, and the actual characteristic, which is detected with the pulsation detection unit.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

As follows, embodiment(s) of the present disclosure will be described with reference to drawings.

1. Configuration

Figure 1:
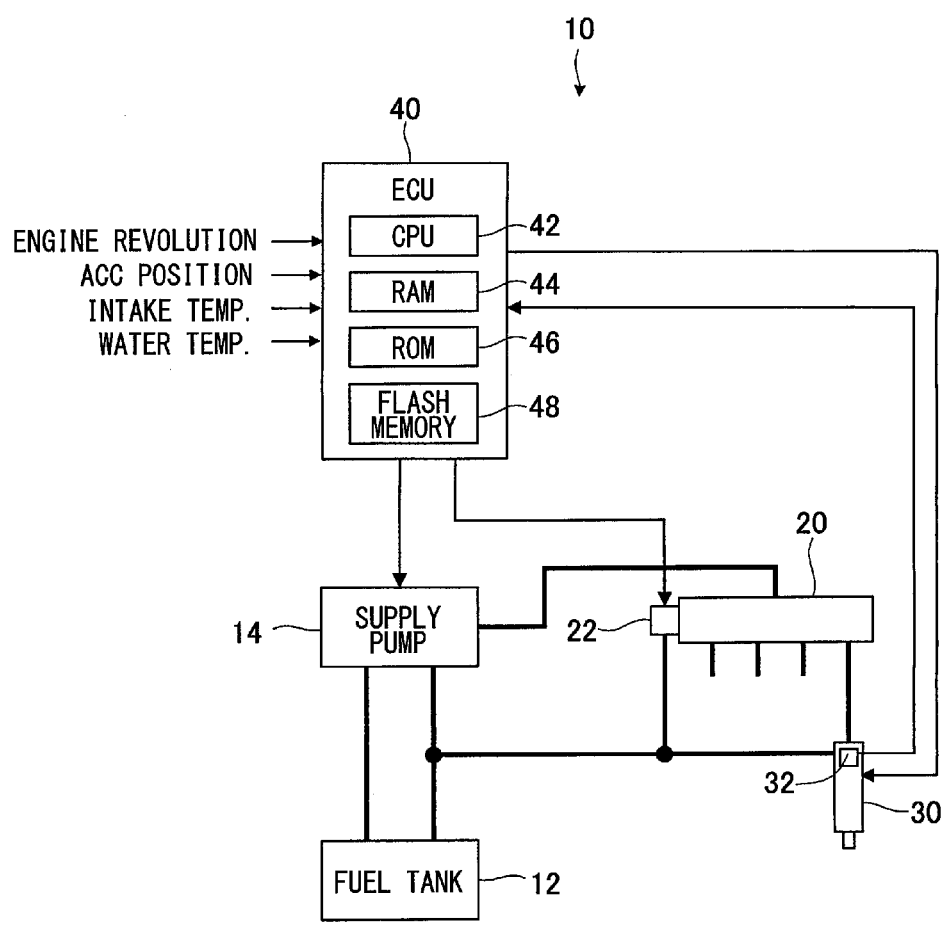
FIG. 1 is a block diagram showing a fuel injection system, which employs a fuel density detection device.

A fuel injection system 10 shown in FIG. 1 is for injecting fuel into an internal combustion engine such as a 4-cylinder diesel engine for an automobile. The fuel injection system 10 includes a fuel supply pump 14, a common rail 20, a fuel injection valve 30, and an electronic control unit (ECU) 40.

The fuel supply pump 14 accommodates a feed pump for pumping fuel from the fuel tank 12. The fuel supply pump 14 may have a general configuration including a plunger, which is movable back and forth with rotation of a cam of a camshaft, thereby to pressurize fuel drawn from the feed pump and to pressure-feed the fuel to a compression chamber.

A metering valve (not shown) meters an amount of fuel discharged from the fuel supply pump 14. More specifically, an electric current supplied to the metering valve is controlled to manipulate an amount of fuel, which is drawn by each plunger of the fuel supply pump 14 in an admission stroke, or to manipulate an amount of fuel, which is pressure-fed by each plunger of the fuel supply pump 14 in a pressure feed stroke. In this way, the metering valve controls the amount of fuel discharged from each plunger of the fuel supply pump 14.

The common rail 20 is a hollow accumulator pipe. The common rail 20 functions as a pressure accumulator to hold pressure of fuel discharged from the fuel supply pump 14. A pressure regulator valve 22 is a solenoid valve equipped to the common rail 20. The pressure regulator valve 22 opens to discharge fuel, which is accumulated in the common rail 20, into a low-pressure component. The pressure regulator valve 22 is manipulated to open to discharge fuel in the common rail 20. In this way, pressure of fuel, which is supplied from the common rail 20 into the fuel injection valve 30, decreases.

The fuel injection system 10 is equipped with various sensors to detect an engine operation state. Specifically, the sensors may include a rotation speed sensor, an accelerator sensor, a temperature sensor, and/or the like. The rotation speed sensor detects an engine rotation speed (NE). The accelerator sensor detects an accelerator position (ACCP), which corresponds to an operation quantity of the accelerator pedal manipulated by a driver. The temperature sensor may detect temperature (water temperature) of cooling water and/or temperature (intake air temperature) of intake air.

The fuel injection valve 30 is equipped to each cylinder of the engine. The fuel injection valve 30 injects fuel, which is pressure-accumulated in the common rail 20, into the corresponding cylinder. The fuel injection valve 30 may be, for example, a generally-used injection valve configured to control a lift of a nozzle needle with application of pressure in a control chamber thereby to open and close an injection hole. An injection quantity of fuel injected from the fuel injection valve 30 is controlled according to a pulse width of an injection instruction signal sent from the ECU 40. Specifically, when the pulse width of the injection instruction signal increases, the injection quantity may increase.

The fuel injection valve 30 includes a pressure sensor 32. The pressure sensor 32 detects pressure of fuel supplied from the common rail 20 to the fuel injection valve 30. The ECU 40 is mainly configured with a microcomputer equipped with, for example, a CPU 42, a RAM 44, a ROM 46, a flash memory 48, and/or the like. The ECU 40 implements various controls of the fuel injection system 10 according to sensor signals sent from various sensors including the pressure sensor 32. The CPU 42 executes a control program, which is stored in the ROM 46 and/or the flash memory 48.

For example, the ECU 40 controls an amount of electricity supplied to the metering valve of the fuel supply pump 14 such that the fuel pressure, which is detected with the pressure sensor 32, is maintained at a target pressure. In this way, the ECU 40 meters the amount of fuel discharged from the fuel supply pump 14.

In addition, the ECU 40 controls various parameters such as a fuel injection quantity, a fuel injection time point of the fuel injection valve 30, and/or the like. The ECU 40 further controls a pattern of multi-stage injection to implement pilot injection before main injection and to implement post-injection after main injection. The ECU 40 stores an injection characteristic data map in the ROM 46 and/or the flash memory 48 for each predetermined range of pressure detected with the pressure sensor 32. The injection characteristic data map represents a correlation between a pulse width of an injection instruction signal, which is to instruct the fuel injection valve 30 to inject fuel, and an injection quantity. The ECU 40 determines an injection quantity of the fuel injection valve 30 according to the accelerator position and/or the engine rotation speed. The ECU 40 further retrieves a pulse width of the injection instruction signal from the injection characteristic data map related to the pertinent range of the fuel pressure, which is detected with the pressure sensor 32. In this way, the ECU 40 retrieves the pulse width to instruct the fuel injection valve 30 to inject fuel by the determined quantity.

A viscosity and a combustion property of fuel, which is supplied into the fuel injection valve 30, may change according to a fuel density. Therefore, the ECU 40 corrects various engine control parameters according to the fuel density. As described later, the present embodiment employs a configuration to detect a fuel density without using a density sensor, which is to detect the fuel density.

Pressure Pulsation

Subsequently, pressure pulsation, which is caused in fuel supplied to the fuel injection valve 30, will be described. The pressure pulsation may occur due to abrupt change in fuel pressure attributed to fuel injection implemented with the fuel injection valve 30.

Figure 2:
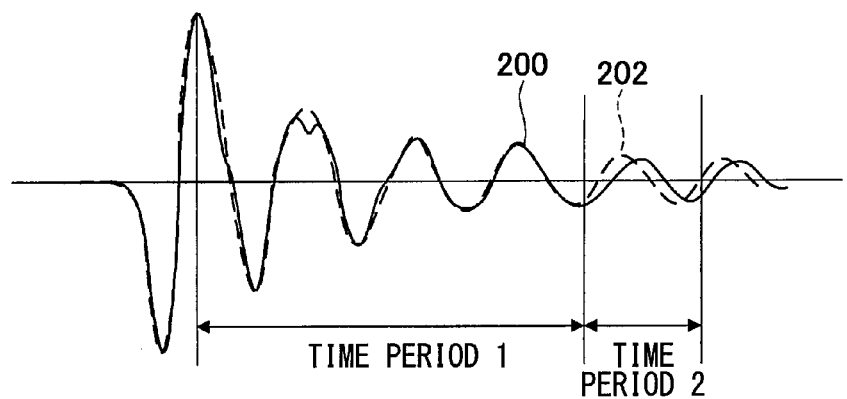
FIG. 2 is a waveform showing a quantity of deviation between a reference pulsation and a pressure pulsation.

Specifically, as shown by a solid line in FIG. 2, when the fuel injection valve 30 injects fuel, fuel pressure changes abruptly to cause a pressure pulsation 200. The pressure pulsation 200 is attenuated as the time elapses. The pressure pulsation 200 shows an actual pressure pulsation caused by fuel injection. To the contrary, a dotted line in FIG. 2 represents a reference pulsation 202. The reference pulsation 202 is pulsation in pressure caused in fuel, which is at a predetermined reference fuel density.

The ECU 40 stores information on the reference pulsation 202 in the ROM 46 and/or the flash memory 48. The information on the reference pulsation 202 may be an equation of a damped oscillation of the reference pulsation 202. The equation may define a function including a fuel pressure and a fuel temperature as parameters. The information on the reference pulsation 202 may be waveform data of a damped oscillation of the reference pulsation 202 correlated with various fuel pressures and/or various fuel temperatures. In view of a data volume of the information on the reference pulsation 202, the equation of a damped oscillation may be employable to reduce an amount of data occupying a data storage.

In FIG. 2, a deviation arises between the waveform of the reference pulsation 202 and the waveform of the pressure pulsation 200. The deviation causes a phase difference on a time axis (time basis). At the same fuel pressure and at the same fuel temperature, the deviation arises due to the difference between a density of fuel causing the reference pulsation 202 and a density of fuel causing the pressure pulsation 200. Subsequent to occurrence of the pressure pulsation 200, as the time elapses, the phase difference between the pressure pulsation 200 and the reference pulsation 202 becomes greater.

To the contrary, as the time elapses further, the amplitude of the pressure pulsation 200 is attenuated. Therefore, as the time elapses further, it becomes more difficult to detect the amount of deviation between the reference pulsation 202 and the pressure pulsation 200. According to the present embodiment, the phase difference between the reference pulsation 202 and the pressure pulsation 200 is detected in one cycle in a time period 2. The one cycle in the time period 2 follows three cycles or four cycles in a time period 1, which is subsequent to occurrence of the pressure pulsation 200. The time period 1 may be beforehand determined according to a result of an experiment implemented on each fuel injection system 10.

Figure 3:
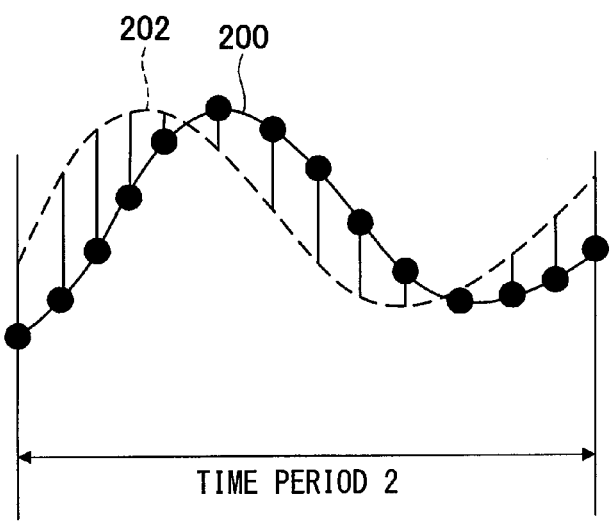
FIG. 3 is an enlarged view showing the deviation between the reference pulsation and the pressure pulsation.

As shown in FIG. 3, the ECU 40 computes an average value of the phase difference between the reference pulsation 202 and the pressure pulsation 200 at each of multiple time points in the time period 2. In this way, the ECU 40 detects the phase difference between the reference pulsation 202 and the pressure pulsation 200. The ECU 40 utilizes a least-square method to compute the movement of the pressure pulsation 200 when the movement of the reference pulsation 202 relative to the pressure pulsation 200 becomes the minimum on the time axis. In this way, the ECU 40 retrieves the computed result as a detection result of the phase difference between the reference pulsation 202 and the pressure pulsation 200.

Figure 4:
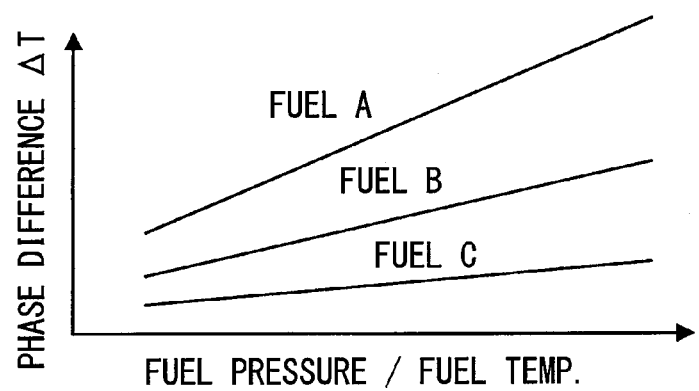
FIG. 4 is a graph showing a relation between a phase difference, which is between a reference pulsation and a pressure pulsation, and a fuel pressure or a fuel temperature for each of fuels, which are difference in the fuel density.

FIG. 4 shows a change characteristic of the phase difference ($\Delta T$) between the reference pulsation 202 and the pressure pulsation 200 when one of the fuel pressure and the fuel temperature does not change and when the other of the fuel pressure and the fuel temperature changes. Fuel A, fuel B, and fuel C are different in the fuel density. Fuel A, fuel B, and fuel C show difference in the phase difference relative to change in the fuel pressure or change in the fuel temperature.

In general, the rate of increase in the phase difference relative to the fuel pressure or the fuel temperature decreases, as the fuel density increases, and increases, as the fuel density decreases. In consideration of this, the relation between the phase difference and the fuel pressure or the relation is approximated with a straight line. The inclination of the straight line for used fuel is detected. Thus, the fuel density of used fuel can be detected according to the inclination of the straight line. The inclination of the straight line decreases, as the fuel density increases. The inclination of the straight line increases, as the fuel density decreases.

The fuel density of used fuel may be detected according to, in replace of the inclination of the straight line, difference between the phase differences at predetermined two points of the fuel pressure or the fuel temperature. Specifically, the fuel density of used fuel may be detected according to the phase difference at predetermined one point of the fuel pressure or the fuel temperature and the phase difference at predetermined another point of the fuel pressure or the fuel temperature. The difference of the phase differences at the two points decreases, as the fuel density increases, and increases, as the fuel density decreases.

Figure 5:
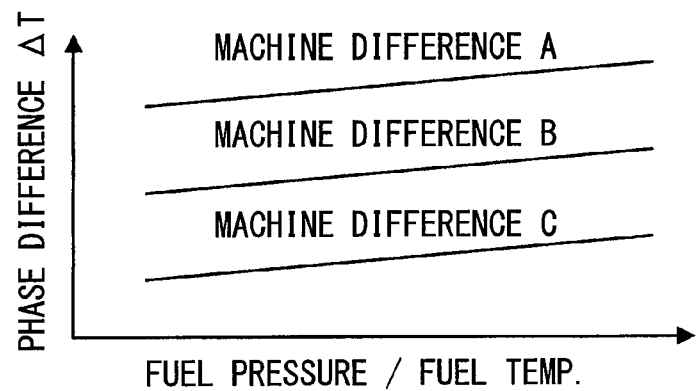
FIG. 5 is a graph showing a relation between a phase difference, which is between a reference pulsation and a pressure pulsation, and a fuel pressure or a fuel temperature among machine differences in a high-pressure passage.

It is noted that, as shown in FIG. 5, it is assumable that, in the high-pressure passage to supply fuel from the common rail 20 to the fuel injection valve 30, the length of the fuel pipe, which is to supply fuel to the fuel injection valve 30, and/or the diameter of an orifice, which is equipped to an outlet of the common rail 20, vary among machine differences A, B, and C. In this assumption, even in a case where the fuel density is the same (constant), the phase differences may vary according to the machine differences A, B, and C. For example, as the length of the fuel pipe increases, the cycle of pressure pulsation increases. Therefore, the phase difference increases.

It is further noted that, in a case where the fuel density is the same, the phase difference may vary among the machine difference A, B, and C, nevertheless, the inclination of the straight line, which represents the relation between the phase difference and the fuel pressure or the fuel temperature, may not change among the machine differences A, B, and C. The reason of this is as follows. Even in a case where the length of the fuel pipe or the diameter of the orifice vary among the machine difference A, B, and C, the characteristic of propagation of the pressure pulsation 200 through fuel may not change on the premise of the same fuel density.

Therefore, the detection of the inclination of the straight line, which represents the relation between the phase difference and the fuel pressure or the fuel temperature, enables to detect the fuel density of used fuel without influence of the variation among the machine difference A, B, and C. Alternatively, the detection of the difference between the phase differences at two predetermined points of the fuel pressure or the fuel temperature enables to detect the fuel density of used fuel without influence of the variation among the machine difference A, B, and C.

2. Processing

Figure 6:
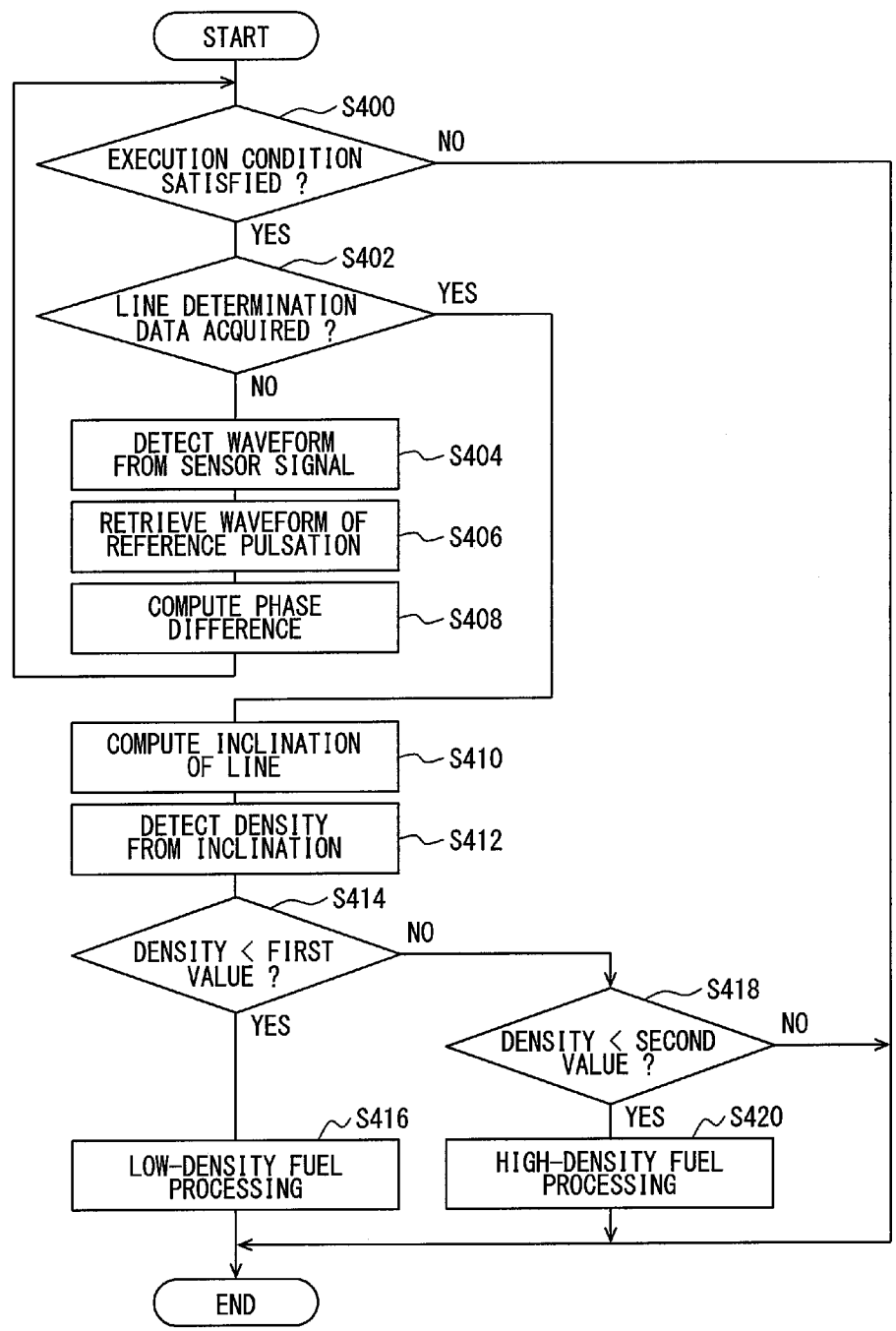
FIG. 6 is a flowchart showing a fuel density detection processing.

A fuel density detection processing will be described with reference to a flowchart in FIG. 6. The fuel density detection processing is executed by the ECU 40. The fuel density detection processing is executed once in one combustion cycle. In FIG. 6, S represents a step.

At S400, the ECU 40 determines that an execution condition of the fuel density detection processing, which is based on pertinent injection, is satisfied when any one of the following conditions is satisfied.

(1) Injection is a single-stage injection.

(2) An interval time between the first-stage injection and a second-stage injection is long enough, when the injection is a multi-stage injection.

(3) It is a single-stage injection implemented for injection quantity learning during a deceleration driving operation.

In the case of (2), the fuel density detection processing is executed in the first-stage injection among the multi-stage injection.

When the execution condition of the fuel density detection processing is satisfied (S400: Yes), the processing proceeds to S402. At S402, it is determined whether data is already acquired. The data at S402 is to determine the inclination of the straight line, which represents the relation between the phase difference and the fuel pressure or the fuel temperature, as shown in FIG. 4. In order to determine the inclination of the straight line, the detection data of the phase differences may be acquired at two or more different points of one of the fuel pressure and the fuel temperature, in a state where the other of the fuel pressure and the fuel temperature is constant.

When acquisition of the linear determination data is not completed (S402: No), the ECU 40 detects a waveform of a pressure pulsation from a sensor signal from the pressure sensor 32 (S404). The ECU 40 may acquire the waveform of the reference pulsation, which corresponds to the fuel pressure and the fuel temperature at this time, by using, for example, an equation of a damped oscillation (S406).

After a predetermined time elapses subsequent to occurrence of the pressure pulsation, the average of the phase differences is computed (S408). The computed average of the phase differences is in, for example, one cycle of the pressure pulsation subsequent to 3 or 4 cycles of the pressure pulsation from the occurrence. The average of the phase differences is computed by calculating an average of the phase differences by utilizing a least-square method at multiple time points as shown in FIG. 3. Thus, the processing is returned to S400.

When acquisition of the linear determination data is completed (S402: Yes), the ECU 40 computes the inclination of the straight line, which represents the relation between the phase difference and the fuel pressure or the fuel temperature (S410). The ECU 40 stores, in the ROM 46 or the flash memory 48, data map, which represents a correspondence between the inclination of the straight line and the fuel density. The ECU 40 detects the fuel density according to the inclination of the straight line with reference to the data map (S412).

When the fuel density is lower than a first predetermined value (S414: Yes), the viscosity of fuel decreases, and consequently, lubricity to fuel decreases. Therefore, the ECU 40 executes the following engine control operations in response to the low-density fuel (S416).

(1) The ECU 40 controls a discharge amount of the fuel supply pump 14 thereby to decrease the maximum pressure of the fuel pressure to be lower than that in a normal condition.

(2) The ECU 40 reduces the maximum revolution of the engine to be lower than that in the normal condition.

When the fuel density is higher than a second predetermined value, which is greater than the first predetermined value (S418: Yes), the viscosity of fuel increases. Consequently, the high-density fuel becomes viscous to be hardly burned. In this case, the processing proceeds to S420 at which the ECU 40 implements the following engine control operations in response to the high-density fuel.

(1) The ECU 40 increases an injection period of the fuel injection valve 30 to be longer than that in the normal condition.

(2) The ECU 40 reduces the number of stages of multi-stage injection in response to increase in the injection period.

When the fuel density is greater than or equal to the first predetermined value and when the fuel density is less than or equal to the second predetermined value (S416: No, S418: No), the ECU 40 implements a normal engine control operation.

3. Effect

The above-described embodiment may produce following effects.

(1) After elapse of the predetermined time subsequent to occurrence of the pressure pulsation, the deviation between the waveform of the reference pulsation and the waveform of the pressure pulsation becomes large on the time axis. In this state, the phase difference between the reference pulsation and the pressure pulsation is detected. In this way, the phase difference can be detected with high accuracy. The present configuration may enable to detect the fuel density with high accuracy according to the phase difference.

(2) The predetermined time period is after elapse of the predetermined time subsequent to occurrence of the pressure pulsation. In the predetermined time period, the phase differences between the waveform of the reference pulsation and the waveform of the pressure pulsation is detected at multiple time points, and the average of the phase differences at multiple time points is detected. Therefore, even when the fuel pressure, which is detected with the pressure sensor 32, contains a noise, the present configuration enables to reduce an error attributed to the noise. The present configuration may enable to detect the fuel density with high accuracy according to the phase difference.

(3) The fuel density is detected according to the phase difference, which is a quantity of the deviation between the reference characteristic of the reference pulsation and the actual characteristic of the pressure pulsation. Therefore, the present configuration may enable to detect the fuel density of used fuel, without influence of the variation in the phase difference among the machine differences.

4. Other Embodiment

One embodiment of the present disclosure is described above. It is noted that, the present disclosure is not limited to the above-described embodiment and may employ various embodiments.

(1) In the above embodiment, the fuel density is detected according to the phase difference between the reference pulsation and the pressure pulsation. The phase difference is used as a quantity of the deviation between the reference characteristic and the actual characteristic. The reference characteristic of the reference pulsation is the reference frequency or a physical quantity, which corresponds to the reference frequency. The actual characteristic of the pressure pulsation is the pulsation frequency or a physical quantity, which corresponds to the pulsation frequency. Alternatively or in addition, as the quantity of deviation between the reference characteristic and the actual characteristic, a frequency, a cycle, and/or the like may be employable.

(2) In the above embodiment, the pressure sensor 32, which is equipped in the fuel injection valve 30, is used to detect the pressure of fuel supplied into the fuel injection valve 30. Alternatively or in addition, a pressure sensor may be equipped to the common rail 20 to detect the fuel pressure.

(3) In the above embodiment, the fuel density detection device of the present disclosure is applied to the common rail type diesel engine. Alternatively or in addition, the fuel density detection device of the present disclosure may be applied to a gasoline engine. The fuel density detection device of the present disclosure may be applied to various devices to detect a pressure pulsation caused in pressure of fuel supplied to a fuel injection valve.

(4) In the above-described embodiments, a function implemented with a singular component (element) may be shared by multiple components, and a function shared by multiple components may be implemented with a singular component. At least a part of the configuration of the above-described embodiments may be replaced with a generally-known configuration, which possesses the same function or a similar function. A part of the configuration of the above-described embodiments may be omitted. At least a part of the configuration of the above-described embodiments may be added to a configuration of another embodiment or may be used as a replacement in a configuration of another embodiment. The present disclosure may incorporate various technical concepts related to embodiments of the present disclosure.

(5) In addition to or alternative to the above-described fuel density detection device, various embodiments may render the present disclosure. For example, the present disclosure may incorporate embodiments such as a fuel injection system, which employs the fuel density detection device as a component, a program product, which is executed by a computer to function as the fuel density detection device, a non-transitory storage medium configured to store the program product, a fuel density detection method, and/or the like.

According to the present disclosure, the density detection device may include the pulsation detection unit, the storage unit, and the density detection unit. The pulsation detection unit may detect, as the actual characteristic, the pulsation frequency of the pressure pulsation, which is caused in the fuel pressure, or the physical quantity corresponding to the pulsation frequency, according to the sensor signal of the pressure sensor. The pressure sensor may be configured to detect the fuel pressure of fuel supplied to the fuel injection valve, which is equipped to the internal combustion engine. The storage unit may be configured to store, as the reference characteristic, the reference frequency of the predetermined reference pulsation or the physical quantity corresponding to the reference frequency.

The density detection unit may be configured to detect the fuel density according to the quantity of deviation between the reference characteristic, which is stored in the storage unit, and the actual characteristic, which is detected with the pulsation detection unit. The present configuration may detect the fuel density according to the quantity of deviation between the reference characteristic of the reference pulsation and the actual characteristic of the pressure pulsation. Therefore, even when the sensor signal of the pressure sensor contain a noise to cause an error in the actual characteristic of the pressure pulsation, which is detected with the pulsation detection unit, an influence of the error of the actual characteristic exerted on the quantity of deviation between the reference characteristic and the actual characteristic may become indirect. Therefore, the present configuration may enhance the accuracy of detection of the fuel density compared with a configuration, which is to detect the fuel density according to only the actual characteristic of the pressure pulsation.

It is noted that, the phase difference, which is between the reference pulsation and the pressure pulsation, is small immediately after occurrence of the pressure pulsation and becomes larger after a time period elapses. Therefore, a configuration may be employable to detect, as the quantity of deviation between the reference characteristic and the actual characteristic, the phase difference between the reference pulsation and the pressure pulsation, after elapse of the predetermined time subsequent to occurrence of the pressure pulsation. That is, the pressure pulsation first occurs, and subsequently, the predetermined time elapses, and at this time, the quantity of deviation may be detected. The present configuration may enable to detect the fuel density with high accuracy according to the large phase difference between the reference pulsation and the pressure pulsation.

The above processings such as calculations and determinations may be performed by any one or any combinations of software, an electric circuit, a mechanical device, and the like. The software may be stored in a storage medium, and may be transmitted via a transmission device such as a network device. The electric circuit may be an integrated circuit, and may be a discrete circuit such as a hardware logic configured with electric or electronic elements or the like. The elements producing the above processings may be discrete elements and may be partially or entirely integrated.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A fuel density detection device comprising:
   a pulsation detection unit configured to detect, as an actual characteristic, a pulsation frequency of a pressure pulsation, which is caused in a fuel pressure, or a physical quantity, which corresponds to the pulsation frequency, according to a sensor signal from a pressure sensor, the pressure sensor configured to detect the fuel pressure of fuel supplied to a fuel injection valve, which is equipped to an internal combustion engine;
   a storage unit configured to store, as a reference characteristic, a reference frequency of a predetermined reference pulsation or a physical quantity, which corresponds to the reference frequency; and
   a density detection unit configured to detect a fuel density according to a quantity of deviation between the reference characteristic, which is stored in the storage unit, and the actual characteristic, which is detected with the pulsation detection unit.

2. The fuel density detection device according to claim 1, further comprising:
   a phase difference detection unit configured to detect, as the quantity of deviation, a phase difference between the reference pulsation and the pressure pulsation, after elapse of a predetermined time period subsequent to occurrence of the pressure pulsation, wherein
   the density detection unit is further configured to detect the fuel density according to the phase difference, which is detected with the phase difference detection unit.

3. The fuel density detection device according to claim 2, wherein
   the phase difference detection unit is further configured to detect the phase difference according to an average value of a plurality of values, each of which represents the phase difference between the reference pulsation and the pressure pulsation, at a plurality of time points, respectively, after elapse of the predetermined time period.

4. The fuel density detection device according to claim 3, wherein
   the phase difference detection unit is further configured to calculate the average value by utilizing a least-square method to detect the phase difference.

5. The fuel density detection device according to claim 2, wherein
   the storage unit is further configured to store, as the reference characteristic, an equation of a damped oscillation of the reference pulsation, and
   the phase difference detection unit is further configured to detect the phase difference between a waveform of the reference pulsation, which is represented by the equation stored in the storage unit, and a waveform of the pressure pulsation, which is detected, as the actual characteristic, with the pulsation detection unit.

6. The fuel density detection device according to claim 2, wherein
   the storage unit is further configured to store, as the reference characteristic, a waveform of the reference pulsation, and
   the phase difference detection unit is further configured to detect the phase difference between the waveform of the reference pulsation, which is stored in the storage unit, and a waveform of the pressure pulsation, which is detected, as the actual characteristic, with the pulsation detection unit.

7. The fuel density detection device according to claim 1, wherein
the storage unit is further configured to store the reference characteristic corresponding to at least one of a fuel pressure and a fuel temperature, and
the density detection unit is further configured to detect the fuel density according to the quantity of deviation, which is between the reference characteristic stored in the storage unit and the actual characteristic, corresponding to the at least one of the fuel pressure and the fuel temperature when the pulsation detection unit detects the actual characteristic.

8. The fuel density detection device according to claim 7, wherein
the density detection unit is further configured to detect the fuel density according to a change characteristic of the quantity of the deviation, which changes correspondingly to change in the at least one of the fuel pressure and the fuel temperature.

9. The fuel density detection device according to claim 8, wherein
the density detection unit is further configured to approximate the change characteristic with a straight line and to detect the fuel density according to an inclination of the straight line.

10. The fuel density detection device according to claim 8, wherein
the density detection unit is further configured to detect the fuel density according to a difference between the quantity of deviation, which is at one point of the at least one of the fuel pressure and the fuel temperature, and the quantity of deviation, which is at an other point of the at least one of the fuel pressure and the fuel temperature, in the change characteristic.

* * * * *